United States Patent
Dale et al.

(10) Patent No.: US 7,324,842 B2
(45) Date of Patent: Jan. 29, 2008

(54) ATLAS AND METHODS FOR SEGMENTATION AND ALIGNMENT OF ANATOMICAL DATA

(75) Inventors: Anders Dale, Boston, MA (US); Sébastien Gicquel, Cambridge, MA (US)

(73) Assignee: CorTechs Labs, Inc., La Jolla, CA (US)

( * ) Notice: Subject to any disclaimer, the term of this patent is extended or adjusted under 35 U.S.C. 154(b) by 653 days.

(21) Appl. No.: 10/055,256

(22) Filed: Jan. 22, 2002

(65) Prior Publication Data

US 2003/0139659 A1 Jul. 24, 2003

(51) Int. Cl.
*A61B 5/00* (2006.01)

(52) U.S. Cl. ............... 600/407; 600/410; 382/128; 382/130; 382/131

(58) Field of Classification Search ............... 600/407, 600/410, 411, 420, 427, 431, 473, 475; 702/183, 702/189; 378/4, 20, 15, 19; 324/309, 307; 382/128, 131

See application file for complete search history.

(56) References Cited

U.S. PATENT DOCUMENTS

| | | | |
|---|---|---|---|
| 4,734,646 A | 3/1988 | Shenoy et al. | |
| 4,884,566 A | 12/1989 | Mountz et al. | 128/303 B |
| RE33,259 E | 7/1990 | Crooks et al. | |
| 5,218,623 A | 6/1993 | Toki et al. | 378/4 |
| 5,454,019 A | 9/1995 | Migita et al. | 378/15 |
| 5,583,903 A | 12/1996 | Saito et al. | 378/19 |
| 5,590,164 A | 12/1996 | Kawai et al. | 378/4 |
| 5,602,891 A * | 2/1997 | Pearlman | 378/62 |
| 5,617,861 A | 4/1997 | Ross et al. | |
| 5,668,846 A | 9/1997 | Fox et al. | 378/4 |
| 5,672,877 A | 9/1997 | Liebig et al. | 250/363.04 |
| 5,818,231 A | 10/1998 | Smith | |
| 5,951,475 A | 9/1999 | Gueziec et al. | 600/425 |
| 6,023,495 A | 2/2000 | Adler et al. | 378/4 |
| 6,028,907 A | 2/2000 | Adler et al. | 378/4 |
| 6,195,409 B1 | 2/2001 | Chang et al. | 378/20 |

(Continued)

FOREIGN PATENT DOCUMENTS

WO WO 02/43003 5/2002

(Continued)

OTHER PUBLICATIONS

Miller MI, Christensen, G.E., Amit, Y., Grenander, U., Mathematical Textbook of Deformable Neuroanatomies, Proceedings of the National Academy of Sciences USA, 90:11944-11948 (1993).*

(Continued)

*Primary Examiner*—Eleni Mantis Mercader
*Assistant Examiner*—Baisakhi Roy
(74) *Attorney, Agent, or Firm*—Lahive & Cockfield LLP

(57) ABSTRACT

The present invention provides an atlas comprising values representative of magnetic resonance properties of a magnetic resonance (MR) scan and optionally, prior probability data relating to tissue type. Further embodiments of the invention involve a system including an MR scanner and the atlas for use in alignment of an MR scan, such as a localizer scan, to obtain a specific geometry of the data acquired during a subsequent scan. Also, a system includes an MR scanner and the atlas for automatic segmentation of an MR scan. Methods of making and using the atlas and system are also provided.

18 Claims, 12 Drawing Sheets

U.S. PATENT DOCUMENTS

| | | | |
|---|---|---|---|
| 6,374,130 B1* | 4/2002 | Reiman | 600/407 |
| 6,430,430 B1* | 8/2002 | Gosche | 600/410 |
| 6,591,004 B1* | 7/2003 | VanEssen et al. | 382/154 |
| 6,740,883 B1* | 5/2004 | Stodilka et al. | 250/363.04 |
| 6,836,557 B2 | 12/2004 | Tamez-Peña et al. | |
| 6,845,342 B1* | 1/2005 | Basser et al. | 702/183 |
| 2001/0036302 A1* | 11/2001 | Miller | 382/128 |
| 2002/0042563 A1* | 4/2002 | Becerra et al. | 600/407 |
| 2002/0103428 A1* | 8/2002 | deCharms | 600/410 |
| 2003/0011624 A1* | 1/2003 | Ellis | 345/646 |
| 2003/0088177 A1 | 5/2003 | Totterman et al. | |
| 2003/0093004 A1* | 5/2003 | Sosa et al. | 600/544 |

FOREIGN PATENT DOCUMENTS

| | | |
|---|---|---|
| WO | WO 03/021524 | 3/2003 |

OTHER PUBLICATIONS

Corbetta, M. et al. "A common network of funtional areas for attention and eye movements." *Neuron*, 21:761-773 (Oct. 1998).

Gusnard, D.A. et al. "Medial prefrontal cortex and self-referential mental activity: relation to a default mode of brain function." *PNAS* 98(7):4259-4264 (Mar. 27, 2001).

Ashburner, J. et al. Image registration using a symmetric prior—in three dimensions. *Hum. Brain Mapp.* Apr. 2000;9(4):212-25.

Brey, W. W. et al. Correction for intensity falloff in surface coil magnetic resonance imaging. *Med. Phys.* Mar.-Apr. 1988;15(2):241-5.

Chen, M. et al. Anomaly detection through registration. http://www.ri.cmu.edu/pub_files/pub1/chen_mei_1998_5/chen_mei_1998_5.pdf.

Chen, M. et al. Anomaly detection through registration. *IEEE Computer Society Conference on Computer Vision and Pattern Recognition.* 1998. pp. 304-310.

Choi, H. S. et al. Partial volume tissue classification of multichannel magnetic resonance images—A mixel model. *IEEE Transactions on Medical Imaging.* Sep. 1991;10(3):395-407.

Clarke, L. P. et al. MRI: stability of three supervised segmentation techniques. *Magn. Reson. Imaging.* 1993;11:95-106.

Clarke, L. P. et al. MRI segmentation: methods and applications. *Magn. Reson. Imaging.* 1995;13(3):343-68.

Collins, D. L. et al. Automatic 3-D model-based neuroanatomical segmentation. *Hum. Brain Mapp.* 1995;3(3):190-208.

Collins, D. L. et al. Animal: validation and applications of nonlinear registration-based segmentation. *International Journal of Pattern Recognition and Artificial Intelligence.* 1997;11(8):1271-94.

Condon, B. R. et al. Image non-uniformity in magnetic resonance imaging: its magnitude and methods for its correction. *Br. J. Radiol.* Jan. 1987;60(709):83-7.

Dawant, B. M. et al. Correction of intensity variations in MR images for computer-aided tissue classification. *IEEE Transactions on Medical Imaging.* Dec. 1993;12(4):770-81.

CorTechs. http://www.cortechs.net Last update Jun. 12, 2001 http://www.cortechs.net/contact.htm; http://www.cortechs.net/about.htm; http://www.cortechs.net/applications.htm; http://www.cortechs.net/flattening.htm; http://www.cortechs.net/mapping.htm; http://www.cortechs.net/movies.htm.

Freeborough, P. A. et al. Accurate registration of serial 3D MR brain images and its application to visualizing change in neurodegenerative disorders. *J. Comput. Assist. Tomogr.* Nov.-Dec. 1996;20(6):1012-22.

Fischl, B. et al. Whole brain segmentation: Automated labeling of neuroanatomical structures in the human brain. Prepublication received directly from author. Jan. 9, 2001. pp. 1-26.

Fischl, B. et al. Whole brain segmentation: Automated labeling of neuroanatomical structures in the human brain. *Neuron.* Jan. 31, 2002;33(3):341-55.

Gee, J. C. et al. Elastically deforming 3D atlas to match anatomical brain images. *J. Comput. Assist. Tomogr.* Mar.-Apr. 1993;17(2):225-36.

Gee, J. C. et al. Probabilistic matching of brain images. 1995. pp. 1-22 http://citeseer.nj.nec.com/gee95probabilistic.html.

Gee, J. C. et al. Probabilistic matching of brain images. *Proceedings of XIVth International Conference on Information Processing in Medical Imaging*, Ile de Berder, France Jun. 26-30, 1995 pp. 113-125.

Gerig, G. et al. Unsupervised segmentation of 3-D dual-echo MR head data.pp. 1-27 http://citeseer.nj.nec.com/57516.html.

Gerig, G. et al. Unsupervised segmentation of 3-D dual-echo MR head data. *Image and Vision Computing.* Jul./Aug. 1992;10(6):349-60.

Haacke, E. M. et al. Spin density, $T_1$ and $T_2$ quantification methods in MR imaging. In *Magnetic Resonance Imaging, Physical Principles and Sequence Design*, Wiley-Liss, 1999, Chapter 22, pp. 637-667.

Itti, L. et al. Automatic scan prescription for brain MRI. *Magnetic Resonance in Medicine.* 2001; 45:486-94.

Jezzard, P. et al. Sources of distortion in functional MRI data. *Hum. Brain Mapp.* 1999;8:80-5.

Liang, Z. et al. Parameter estimation of finite mixtures using the EM algorithm and information criteria with application to medical image processing. *IEEE Transactions on Nuclear Science.* 1992;39(4):1126-33.

Liang, Z. et al. Parameter estimation and tissue segmentation from multispectral MR images. *IEEE Transactions on Medical Imaging.* Sep. 1994;13(3):441-49.

Liang, Z. et al. Development of automatic techniques for segmentation of brain tissues from multispectral MR images. *IEEE Conf Record IEEE NSS-MIC*, 1995;3:1453-6.

Maes, F. et al. Multimodality image registration by maximization of mutual information. *IEEE Transactions on Medical Imaging.* Apr. 1997;16(2):187-198.

Rajapakse, J. C. et al. Cerebral magnetic resonance image segmentation using data fusion. *J. Comput. Assist. Tomogr.* 1996;20(2):206-18.

Rajapakse, J. C. et al. Statistical approach to segmentation of single-channel cerebral MR images. *IEEE Transactions on Medical Imaging.* Apr. 1997;16(2):176-86.

Simmons, A. et al. Sources of intensity nonuniformity in spin echo images at 1.5 T. *Magn. Reson. Med.* Jul. 1994;32(1):121-8.

Strother, S. C. et al. Quantitative comparisons of image registration techniques based on high-resolution MRI of the brain. *J. Comput. Assist. Tomogr.* Nov.-Dec. 1994;18(6):954-62.

Taxt, T. et al. Multispectral analysis of the brain using Magnetic Resonance Imaging. *IEEE Transactions on Medical Imaging.* Sep. 1994;13(3):470-81.

Thompson, P. M. et al. Mathematical/computational challenges in creating deformable and probabilistic atlases of the human brain. *Hum. Brain Mapp.* Feb. 2000;9(2):81-92.

Vaidyanathan, M. et al. Normal brain volume measurements using multispectral MRI segmentation. *Magn. Reson. Imaging.* 1997;15(1):87-97.

Van Leemput, K. et al. Automated model-based bias field correction of MR images of the brain. *IEEE Transactions on Medical Imaging.* Oct. 1999;18(10):885-96.

Vannier, M. W. et al. Multispectral magnetic resonance image analysis. *CRC Crit. Rev. Biomed. Eng.* 1987;15(2):117-44.

Vannier, M. W. et al. Modeling and data structure for registration to a brain atlas of multimodality images. In *Functional Neuroimaging—Technical Foundations*. Thatcher, R. W. et al. Eds. Academic Press, New York 1994. pp. 217-221.

Wang, Y. et al. Quantification and segmentation of brain tissues from MR images: A probabilistic neural network approach. *IEEE Transactions on Image Processing.* Aug. 1998;7(8):1-12.

Warfield, S. K. et al. Adaptive, template moderated, spatially varying statistical classification. *Medical Image Analysis.* 2000;4:43-55.

Wells, W. M., III et al. Adaptive Segmentation of MRI Data. pp. 1-40 http://citeseer.nj.nec.com/168252.html.

Wells, W. M., III et al. Adaptive Segmentation of MRI Data. *IEEE Transactions on Medical Imaging.* 1996;15(4):429-42.

Wells, W. M., III et al. Adaptive Segmentation of MRI Data. Corrected version pp. 0-40 http://citeseer.nj.nec.com/wells96adaptive.html.

Wells, W. M., III et al. Multi-modal volume registration by maximization of mutual information. pp. 1-20 http://citeseer.nj.nec.com/354937.html.

Wells, W. M., III et al. Multi-modal volume registration by maximization of mutual information. *Medical Image Analysis.* 1996;1(1):35-51.

Wendt, R. E. et al. MR imaging of susceptibility-induced magnetic field inhomogeneities. *Radiology.* Sep. 1988;168(3):837-41.

Fox et al., "*Visualization and Quantification of Rates of Atrophy in Alzheimer's Disease*", The Lancet, vol. 348, Jul. 13, 1996, pp. 94-97.

Crum et al., "*The Use of Regional Fast Fluid Registration of Serial MRI to Quantify Local Change in Neurodegenerative Disease*", Dementia Research Group, Department of Clinical Neurology, Institute of Neurology, London, UK, MIUA99 On-line proceedings, 1999 (4 pages).

Thompson et al., "*Cortical Change in Alzheimer's Disease Detected With a Disease-specific Population-based Brain Atlas*", Cerebral Cortex, Jan. 2001, pp. 1-16.

Dale et al., "*Cortical Surface-Based Analysis*", NeuroImage 9, (1999) pp. 179-194.

Dale, Abstract "*Fully Automated Whole-Brain Segmentation and Morphometric Analysis: A Site-Independent Approach*", http://www.nimh.nih.gov/neuroinformatics/society2001abstracts.cfm, 2001.

J.A.Castelijns, F. Barkhof, "*Magnetic Resonance (MR) Imaging as a Marker for Multiple Sclerosis*", Biomed & Pharmacother, 1999, pp. 351-357.

Laakso et al., "*Hippocampus in Alzheimer's Disease: a 3-year Follow-up MRI Study*", Society of Biological Psychiatry, 2000, pp. 557-561.

G. Calmon, N. Roberts, "*Automatic Measurement of Changes in Brain Volume on Consecutive 3D MR Images by Segmentation Propagation*", Magnetic Resonance and Image Analysis Research Centre, University of Liverpool, Liverpool, UK, 1999, Magnetic Resonance Imaging 18 (2000), pp. 439-453.

Bharatha et al., "*Evaluation of Three Dimensional Finite Element-based Deformable Registration of Pre- and Intra-Operative Prostate Imaging*", Med Phys 28:2551-2560, 2001 (43 pages).

Ferrant et al., "*Registration of 3D Intraoperative MR Images of the Brain Using a Finite Element Biomechanical Model*", In Proceedings of Third International Conference On Medical Robotics, Imaging and Computer Assisted Surgery, Pittsburgh, Pennsylvania, USA. 2000. pp. 19-28.

Ferrant M., "*Physics-Based Deformable Modeling of Volumes and Surfaces for Medical Image Registration, Segmentation and Visualization*", Ph.D. Thesis, Universite Catholique de Louvain, 2001 (143 pages).

Ferrant et al., "*Registration of 3D Intraoperative MR Images of the Brain Using a Finite Element Biomechanical Model*", IEEE Transactions on Medical Imaging, 20:1384-1397 2001, pp. 1-14.

Ferrant et al., "*Surface Based Atlas Matching of the Brain Using Deformable Surfaces and Volumetric Finite Elements*", Proceedings of Medical Image Computing and Computer Aided Intervention (MICCAI) 2001, Springer Verlag, 2001, 2 pages.

Gering et al., "*An Integrated Visualization System for Surgical Planning and Guidance Using Image Fusion and an Open MR*", Journal of Magnetic Resonance Imaging 2001; 13:967-975, pp. 967-975.

Kaus et al., "*Simulation of Corticospinal Tract Displacement in Patients with Brain Tumors*", In Proceedings of Third International Conference On Medical Robotics, Imaging and Computer Assisted Surgery, Pittsburgh, Pennsylvania, USA. 2000. pp. 9-18 (pp. 1-9).

Kaus et al., "*Automated Segmentation of MRI of Brain Tumors*", (Abstract), Radiology 2001; 218(2):586-591 (13 pages).

Leventon M., "*Statistical Models for Medical Image Analysis*", (PostScript), Ph.D. Thesis, MIT, 2000, 156 pages.

Leventon, et al., "*Level Set Based Segmentation with Intensity and Curvature Priors*", Neurosurgery 48:787798, 2001, 8 pages.

Rexilius J., "*Physics-Based Nonrigid Registration for Medical Image Analysis*", Master's Thesis, 2001. Medical University of Luebeck, Germany, 72 pages.

Rexilius J, et al., "*A Novel Nonrigid Registration Algorithm and Applications*", Proceedings of Medical Image Computing and Computer Aided Intervention (MICCAI) 2001, Springer Verlag, 2001, 8 pages.

Rexilius, et al., "*Automatic Nonrigid Registration for Tracking Brain Shift during Neurosurgery*", Workshop Bildverarbeitung fuer die Medizin, Springer Verlag, Heidelberg, Germany, Mar. 2002, p. 135-138 (4 pages).

Ruiz-Alzola et al., "*Nonrigid Registration of 3D Scalar, Vector and Tensor Medical Data*", In Proceedings of Third International Conference On Medical Robotics, Imaging and Computer Assisted Surgery, Pittsburgh, Pennsylvania, USA. 2000. pp. 541-550 (10 pages).

Sperling et al., "*Regional Magnetic Resonance Imaging Lesion Burden and Cognitive Function in Multiple Sclerosis: A longitudinal study*", Arch Neurol. 2001; 58:115-121 (19 pages).

Tei et al., "*Tracking Volumetric Brain Deformations During Image Guided Neurosurgery*", In VISIM: Information Retrieval and Exploration in Large Medical Image Collections, in conjunction with MICCAI 2001, Springer Verlag, 2001 (12 pages).

Tei A., "*Multi-Modality Image Fusion by Real-Time Tracking of Volumetric Brain Deformation During Image Guided Neurosurgery*", Master's Thesis, MIT, 2002 (89 pages).

Fischl et al., "*Whole Brain Segmentation: Automated Labeling of Neuroanatomical Structures in the Human Brain*", Neuron, vol. 33, Issue 3, Jan. 31, 2002 pp. 341-355 (with copy accepted for publication) (44 pages total).

* cited by examiner

|SUBJECT|1|2|3|
|---|---|---|---|
|INTENSITY|100|200|50|
|TISSUE TYPE|1|1|2|

*FIGURE 9A*

| STEP | STEP 1 | STEP 2 | STEP 3 | |
|---|---|---|---|---|
| TISSUE TYPE | 1 | 1 | 1 | 2 |
| MEAN | 100 | 150 | 150 | 50 |
| VARIANCE | 0 | 50 | 50 | 0 |
| PROBABILITY | 1 | 1 | 2/3 | 1/3 |

*FIGURE 9B*

ATLAS AND METHODS FOR SEGMENTATION AND ALIGNMENT OF ANATOMICAL DATA

TECHNICAL FIELD

The present invention generally relates to magnetic resonance and other biological scan data.

BACKGROUND

Magnetic resonance imaging is a complex interaction between protons in biological tissues, a static and alternating magnetic field (the magnet), and energy in the form of radio-frequency waves of a specific frequency (RF), introduced by coils placed next to the subject. The energy state of the hydrogen protons is transiently increased. The subsequent return to equilibrium (relaxation) of the protons results in the release of RF energy which can be measured by the same surface coils that delivered the RF pulses. The RF energy, also referred to as the RF signal or echo, is complex and is thus transformed by Fourier analysis into useful information used to form an MR image.

SUMMARY

The present invention provides apparatus and methods for processing data associated with magnetic resonance (MR) scanning. In particular, in one embodiment, the present invention provides an atlas comprising at least one value representative of a magnetic property and, optionally, at least one value representative of tissue type prior probability. In a further embodiment, the present invention provides an atlas comprising a plurality of values representative of magnetic properties of a plurality of spatial locations of a plurality of subjects. In one embodiment, a system is provided having both an MR scanner and an atlas of the present invention. In a further embodiment, the invention provides methods of making and using the atlas and system.

The apparatus and methods of the present invention provide a model having data representative of one or more subjects. The data includes magnetic property values, optionally, tissue type prior probability values. The atlas can be used to automatically align an MR scan, such as a localizer scan, to obtain a specific geometry of the data acquired during a subsequent scan. The atlas may also be used to automatically identify, or segment, tissue type of a subject based on MR scan data of the subject.

According to one embodiment of the invention, an atlas is provided comprising a plurality of values representative of a magnetic property of a plurality of spatial locations of a subject as determined by magnetic resonance. According to a further embodiment, an atlas is provided comprising values representative of a statistical representation of a magnetic property of a plurality of spatial locations of a plurality of subjects. The present invention also provides a system comprising an MR scanner and an atlas. For example, the atlas may contain magnetic property data. The system can be used to automatically align an MR scan, such as a localizer scan, to obtain a specific orientation of the data acquired during a subsequent scan. The system may also be used to automatically identify, or segment, tissue type of a subject based on MR scan data of the subject.

Methods of using the atlas are further provided herein. In one embodiment, a method of using the atlas having magnetic property values to obtain a specific geometry of data to be acquired during a subsequent scan is provided. In a variation of this embodiment, a method of using the atlas may additionally involve tissue type probabilities.

Methods of using the atlas are further provided herein. In one embodiment, a method of using the atlas having magnetic property values to determine tissue type is provided. In a variation of this embodiment, a method of using the atlas may additionally involve tissue type probabilities.

According to a further embodiment of the invention, a method is provided for obtaining information about a subject having the steps of providing a magnetic resonance scanner, providing an atlas having magnetic resonance data derived from at least one other subject and processing information received from the scanner pertaining to the subject. Also included are the steps of reading the atlas and determining alignment of the magnetic resonance scan to obtain a specific geometry of a subsequent magnetic resonance scan.

According to another embodiment of the invention, another method is provided for obtaining information about a subject. This method involves the steps of providing magnetic property values corresponding to tissue types pertaining to the subject, providing an atlas having magnetic property values derived from at least one other subject, along with labeling tissue types of a tissue corresponding to the magnetic resonance property values pertaining to the subject by using the atlas having the magnetic resonance values derived from at least one other subject.

According to a further embodiment of the invention, a method is provided for creating an atlas by providing a first magnetic resonance modality volume pertaining to a subject, divided into voxels, and recording a magnetic property value in a node of the atlas corresponding to a voxel of the first magnetic resonance modality volume.

Another embodiment of the invention involves a method for creating an atlas. A first magnetic resonance modality volume is provided pertaining to a subject and divided into voxels. A labeled volume is provided indicating tissue types of tissue corresponding to the voxels. Distortion of the first magnetic resonance modality volume is corrected. Magnetic property distribution parameters are extracted for each tissue type identified at each voxel. Also, magnetic property data is recorded corresponding to each tissue type in a node of the atlas corresponding to a voxel of the first magnetic resonance modality volume.

According to another embodiment, a method for creating an atlas is provided wherein a voxel intensity is obtained from an image representative of at least one magnetic modality of a voxel of a subject, a magnetic property value is derived from the voxel intensity, and the magnetic property value is written to a node of the atlas corresponding to the voxel.

A further embodiment of the invention provides a method for processing an image of a subject. An atlas is provided having magnetic property values derived from at least one other subject. The image is aligned to the atlas, and the image is segmented into segments. The segments are labeled to designate a tissue type of a tissue corresponding to the magnetic property values pertaining to the subject by the use of the atlas. An image is thus obtained pertaining to magnetic property values of the subject.

It will further be appreciated that in the methods of the present invention, distortion may be corrected prior to entering the data into the atlas, as well as prior to processing newly acquired data in conjunction with the atlas.

BRIEF DESCRIPTION OF THE DRAWINGS

The invention will be apparent from the description herein and the accompanying drawings, in which like reference characters refer to the same parts throughout the different views.

FIGS. 9A and 9B illustrate sample data for determination of the content of a node of an atlas;

DETAILED DESCRIPTION

Figure 1:
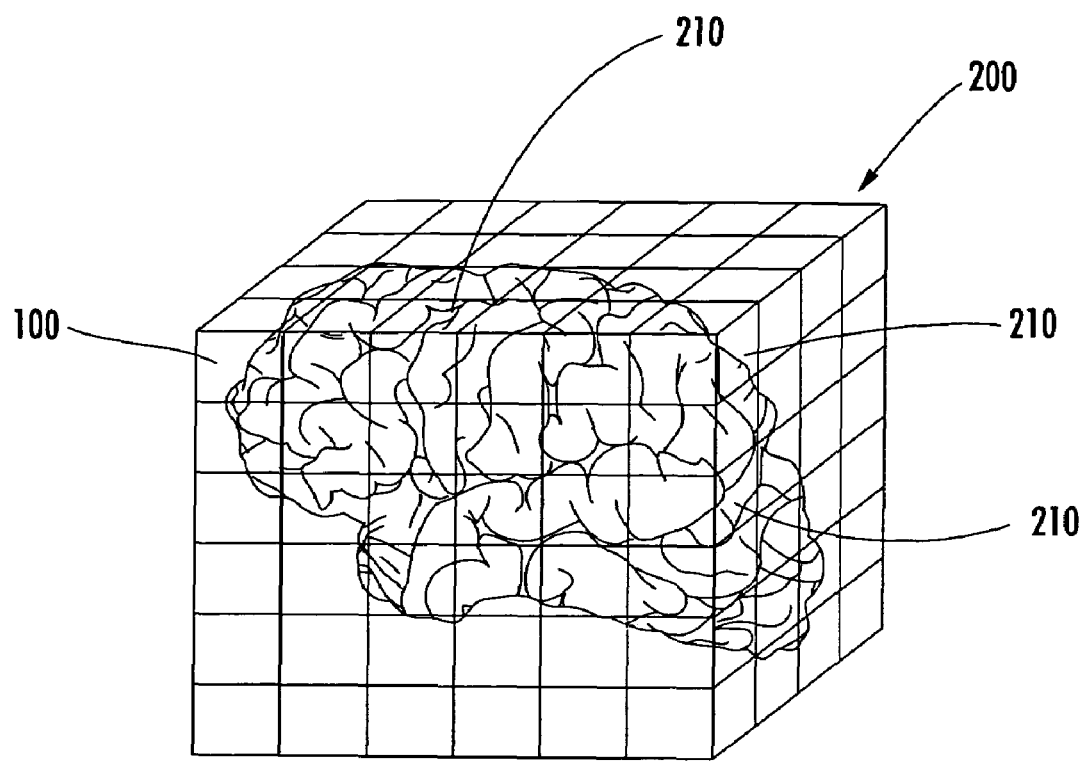
FIG. 1 provides a subject and a grid pattern illustrating voxels of a subject.

The present invention, in various embodiments, involves an atlas containing values representative of magnetic properties of a magnetic resonance (MR) scan and optionally prior probability data relating to tissue type. Further embodiments of the invention involve a system including an MR scanner and the atlas for use, for example, in alignment of an MR scan and for automatic segmentation of an MR scan. Methods of creating and using the atlas and system are also provided.

As used herein, the following terms are defined as follows:

T1 and T2 relaxation times: The rate of return to equilibrium of perturbed protons is referred to as the relaxation rate. The relaxation rate is different for different normal and pathologic tissues. The relaxation rate of a hydrogen proton in a tissue is influenced by surrounding molecular environment and atomic neighbors. Two relaxation rates, the T1 and T2 relaxation times, may be measured. The T1 relaxation rate is the time for 63% of the protons to return to their normal equilibrium state, while the T2 relaxation rate is the time for 63% of the protons to become dephased owing to interactions among adjacent protons. The intensity of the signal and thus the image contrast can be modulated by altering certain parameters, such as the interval between RF pulses (TR) and the time between the RF pulse and the signal reception (TE). So-called T1-weighted (T1W) images are produced by keeping the TR and TE relatively short. Under these conditions, contrast between structures is based primarily on their T1 relaxation differences. T2-weighted (T2W) images are produced by using longer TR and TE times.

TR: The time between repetitions of RF in an imaging sequence.

TE: The time between the RF pulse and the maximum in the echo in a spin-echo sequence.

Flip Angle: The angle that the magnetic moment vector rotates when applying a B1 RF pulse field.

T1: The time to reduce the difference between the longitudinal magnetization and its equilibrium magnetization by an exponential factor.

T2: The time to reduce the transverse magnetization by an exponential factor.

PD: The concentration of spins.

T1-weighted: A magnetic resonance image where the contrast is predominantly dependent on T1.

T2-weighted: A magnetic resonance image where the contrast is predominantly dependent on T2.

PD-weighted: A magnetic resonance image where the contrast is predominantly dependent on PD.

Diffusion-weighted: A magnetic resonance image where the contrast is predominantly dependent on diffusion weighting gradient.

Magnetization Transfer-weighted: A magnetic resonance image where the contrast is predominantly dependent on magnetization transfer saturation effect.

Tissue Type: As used herein, "tissue type" can be used to designate a classification or characteristic of a tissue, such as tissue within a voxel. For example, when used with a human brain as the subject, tissue type can include, without limitation, gray matter, white matter and cerebral spinal fluid. Optionally, the tissue type can be more specific, such as referring to anatomical structure. For example, in the case of a brain as the subject, the tissue type may designate gray matter and/or, more specifically, hippocampus, or other appropriate anatomical structure label. In another example, in the case of a spine as a subject, the tissue type may designate bone, and/or more specifically vertebral bodies, or other appropriate anatomical structure labels. In yet another example, in the case of the kidney as a subject, the tissue type may designate the cortex, and/or more specifically nephrons, or other appropriate anatomical structure labels.

Localizer scan: A low-resolution scan acquired at the beginning of a scanning procedure to estimate the precision of the acquisition geometry relative to the subject to be imaged.

Subsequent scan: A high-resolution scan acquired on the basis of the localizer geometry, such as orientation, dimensions, or voxel size.

Magnetic property: A magnetic property of protons, such as T2, T1, PD, diffusion or magnetization transfer.

The present invention is applicable to a wide variety of MR scans of a subject including mammals (e.g. humans), as well as specific portions of a subject (e.g., organ, limb, or a portion of an organ or limb), also referred to herein as the "subject". Each subject is divided in three-dimensional space into voxels. With reference to FIG. 1, a subject 100, such as a human brain, is shown with an illustrative grid pattern 200 signifying the locations of voxels 210. Each voxel 210 represents a three-dimensional portion of the subject 100. A voxel 210 may be of various dimensions and can have different dimensions along different axes within the subject 100.

Figure 2:
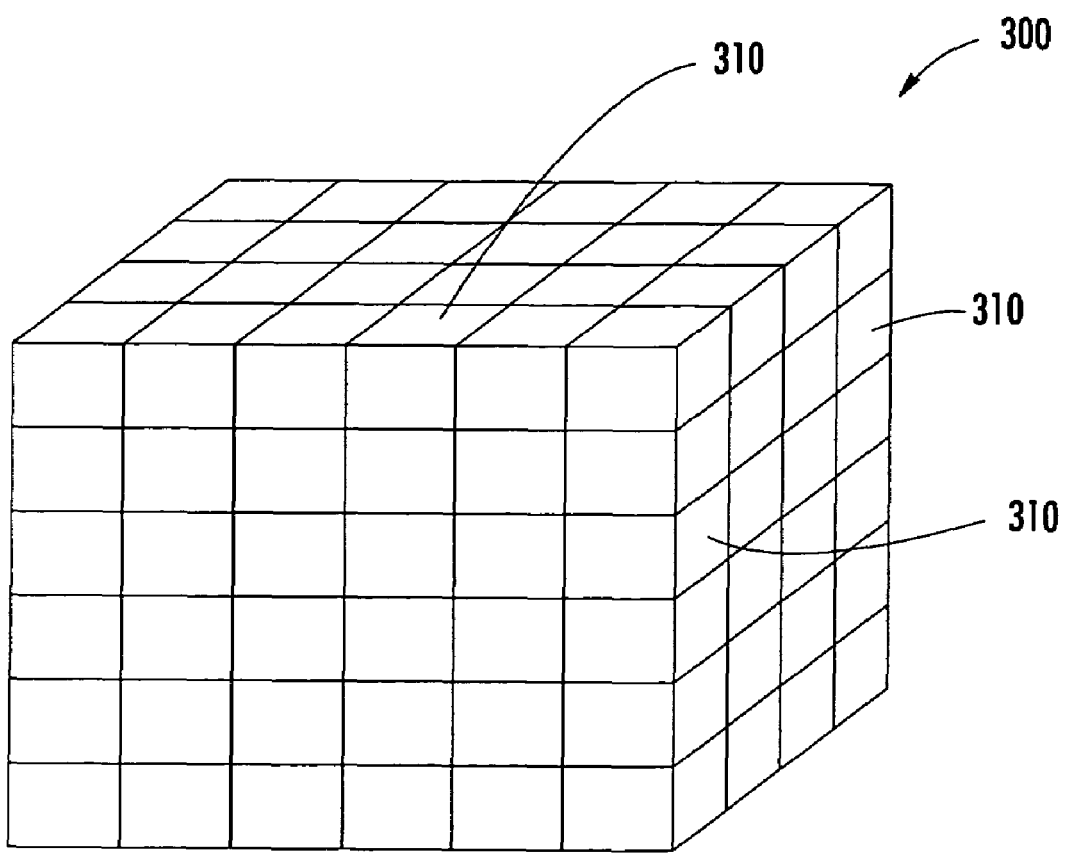
FIG. 2 illustrates an atlas.

As shown in FIG. 2, an atlas 300 is provided according to an embodiment of the invention. While illustrated as a three-dimensional structure, the invention is not so limited, as the atlas 300 may be formed of any of a variety of data structures as will be apparent to one of ordinary skill in the art. The atlas 300 includes nodes 310. According to an embodiment of the invention, each node 310 corresponds to a voxel 210 (of. FIG. 1) representing a portion of the subject 100. Alternatives of the invention may involve fewer nodes 310 than voxels 210. In such a case, a node 310 may be configured to represent a plurality of voxels 210 or the nodes 310 may represent only a subset of the overall voxels 210.

Figure 3:
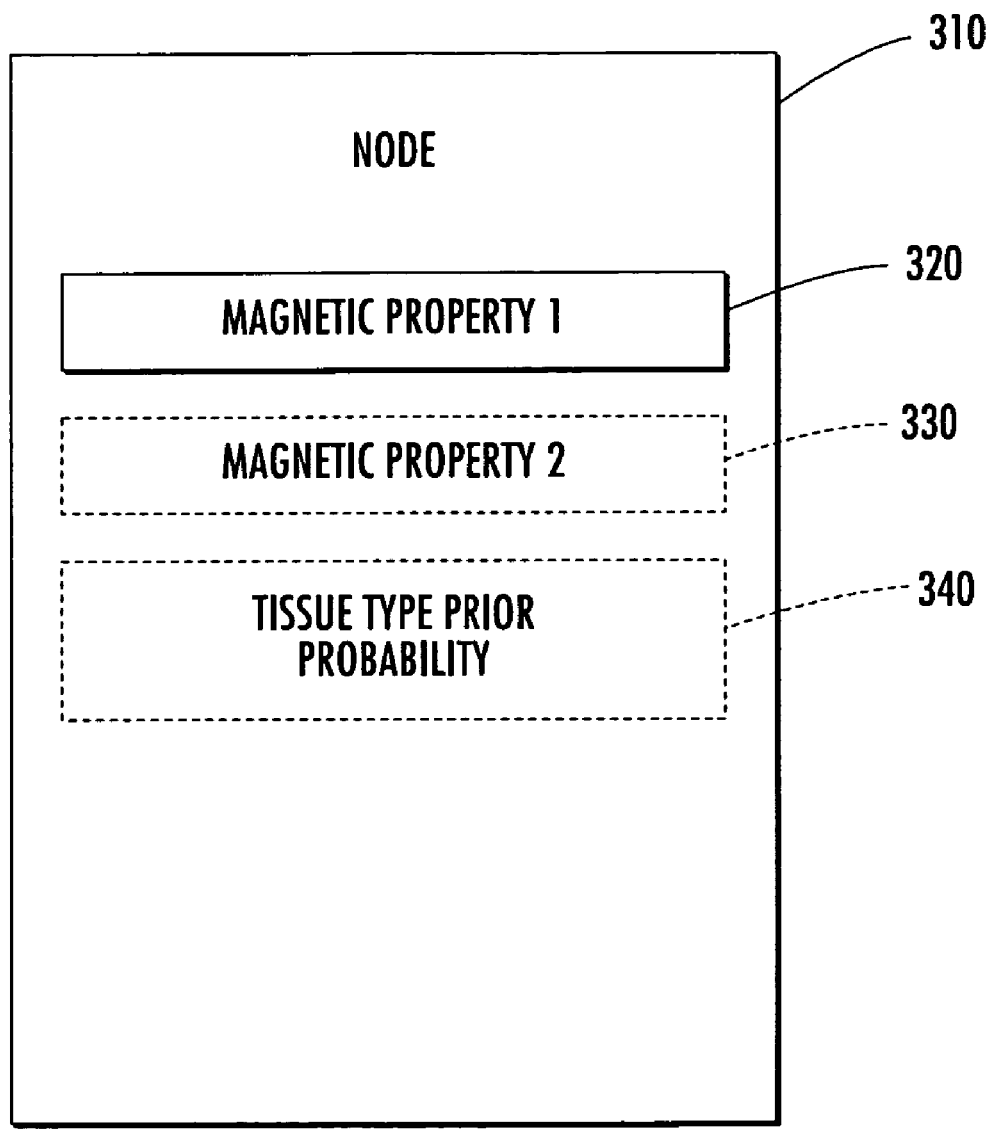
FIGS. 3-8 illustrate nodes of an atlas according to various embodiments of the invention.

FIGS. 3-8 provide various configurations of the nodes 310 according to alternative embodiments of the invention. Each node 310 is configured to store information relating to the corresponding voxel 210. As shown in FIG. 3, the node 310 may be configured to have a magnetic property 320 corresponding to the voxel 210. magnetic properties may include, but are not limited to, T1, T2, proton density (PD), T2*, magnetization transfer, diffusion tensor and derived variables, such as anisotropy and diffusivity. According to one embodiment of the invention, the magnetic properties may be computed from the images, based on a forward model, and the MR acquisition parameters, including, but not limited to, TR, TE, and flip angle. Determination of such magnetic properties and details regarding the MR acquisition parameters can be found in *Magnetic Resonance Imaging, Physical Principle and Sequence Design*, E. M. Haacke et al., Wiley-Liss, 1999, pp. 637-667, which is incorporated herein by reference.

Optionally, a second magnetic property 330 corresponding to the voxel 210 may also be stored in the node 310. Additional magnetic properties may also be stored in the node 310.

A tissue type prior probability 340 corresponding to a tissue type found in the voxel 210 may optionally be stored in the node 310. When used with a human brain as the subject, tissue type can include, without limitation, gray matter, white matter and cerebral spinal fluid. Optionally, the tissue type can be more specific, such as referring to anatomical structure. For example, in the case of a brain as the subject, the tissue type may designate gray matter and/or, more specifically, the hippocampus, or other appropriate anatomical structure label. In another example, in the case of the spine as a subject, the tissue type may designate bone, and/or more specifically vertebral bodies, or other appropriate anatomical structure labels. In yet another example, in the case of the kidney as a subject, the tissue type may designate the cortex, and/or more specifically nephrons, or other appropriate anatomical structure labels. It will be appreciated that the tissue type of the voxel 210 may be determined by human labeling or may be determined by other known methods such as an algorithm (e.g. *Adaptive Segmentation of MRI Data*, Wells W M, at al., *IEEE Transactions on Medical Imaging*, 1996;15:429-442 (corrected version available at http://citeseer.nj.nec.com/cache/papers/cs/19782/http: zSzzSzsplweb.bwh.harvard.edu:80 00zSzpageszSzp-plzSzswzSzpaperszSztmi-96.pdf/wells96adaptive.pdf), *Statistical Approach to Segmentation of Single-Channel Cerebral MR Images*, Rajapakse J C, et al., *IEEE Transactions on Medical Imaging*, 1997, Vol. 16, No.2: 176-86, and *Automated Model-Based Bias Field Correction of MR Images of the Brain*, Van Leemput, K. et al., *IEEE Transactions on Medical Imaging*, 1999, Vol. 18, No. 10), which are incorporated herein by reference.

Figure 4:
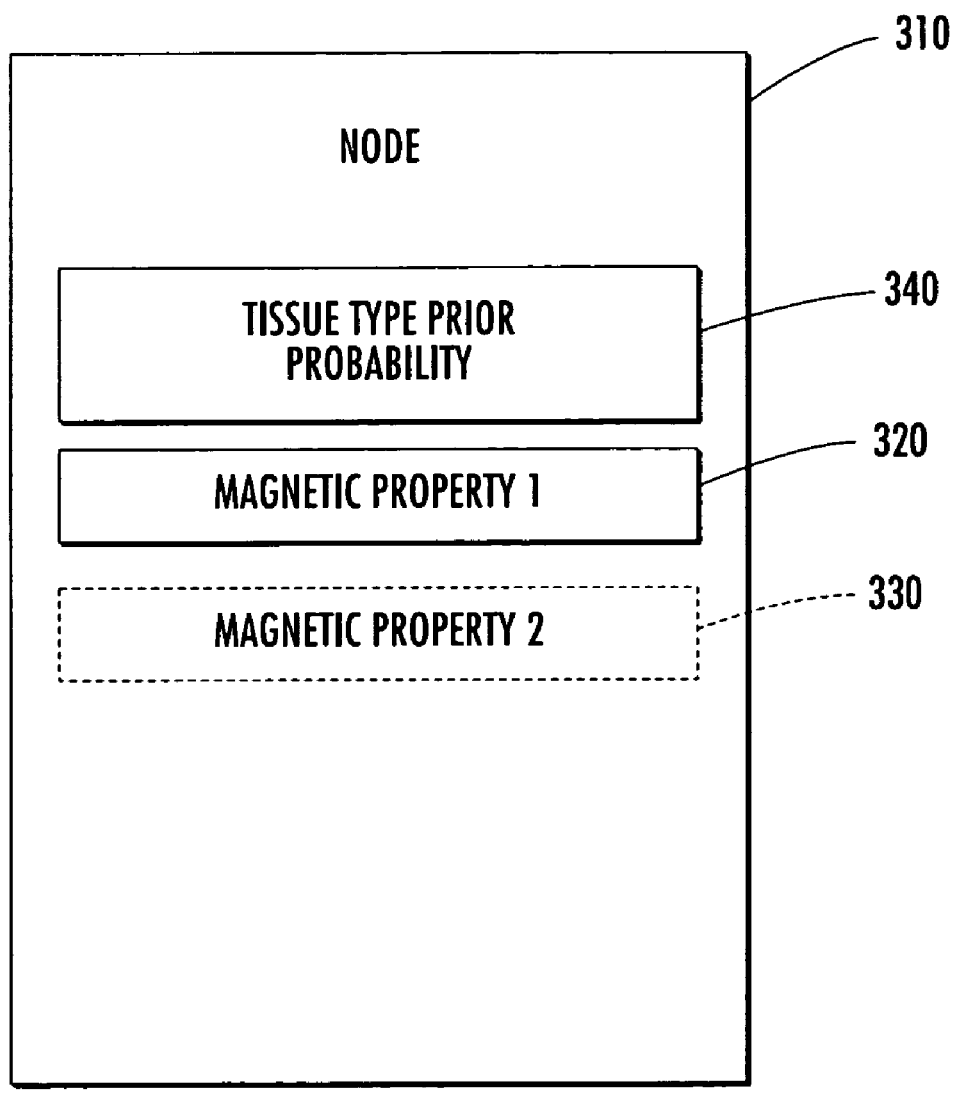

According to a further embodiment of the invention, a node 310 may include a tissue type prior probability 340 corresponding to a tissue type found in the voxel 210, as illustrated in FIG. 4. According to this embodiment, a first magnetic property 320 is also stored. Optionally, a second magnetic property 330, or additional magnetic properties, may also be stored in the node 310.

Figure 5:
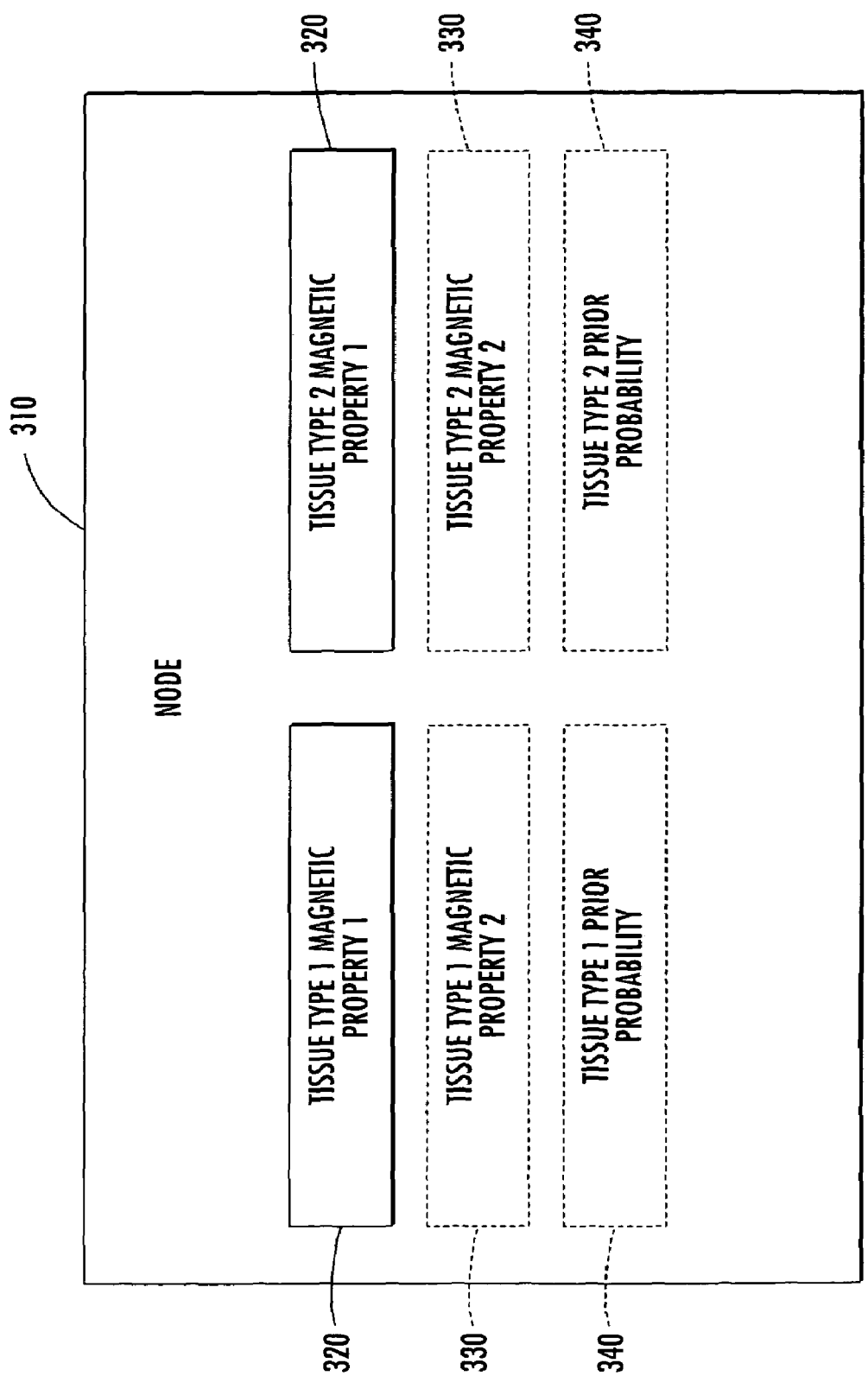

According to a further embodiment of the invention, as shown in FIG. 5, one or multiple magnetic properties may be determined for each of the tissue types located at the corresponding voxel 210. Therefore, as shown by way of example in FIG. 5, if a voxel 210 has two tissue types located at the voxel 210, as determined from a plurality of subjects, one or more magnetic properties 320, 330 may be stored for each of the tissue types. As shown in FIG. 5, a value of a first magnetic property 320 may be stored for the tissue type 1 at the corresponding voxel. Optionally, a value of a second magnetic property 330 may also be stored for tissue type 1. Separate magnetic properties 320, 330 may also be stored for the values corresponding to the tissue of tissue type 2. This variation of the invention is useful in conjunction with an atlas 300 formed of information from more than one subject 100. A tissue type probability 340 may also be optionally stored in the node 310 for one or more of the tissue types detected at the corresponding voxel 210.

Figure 6:
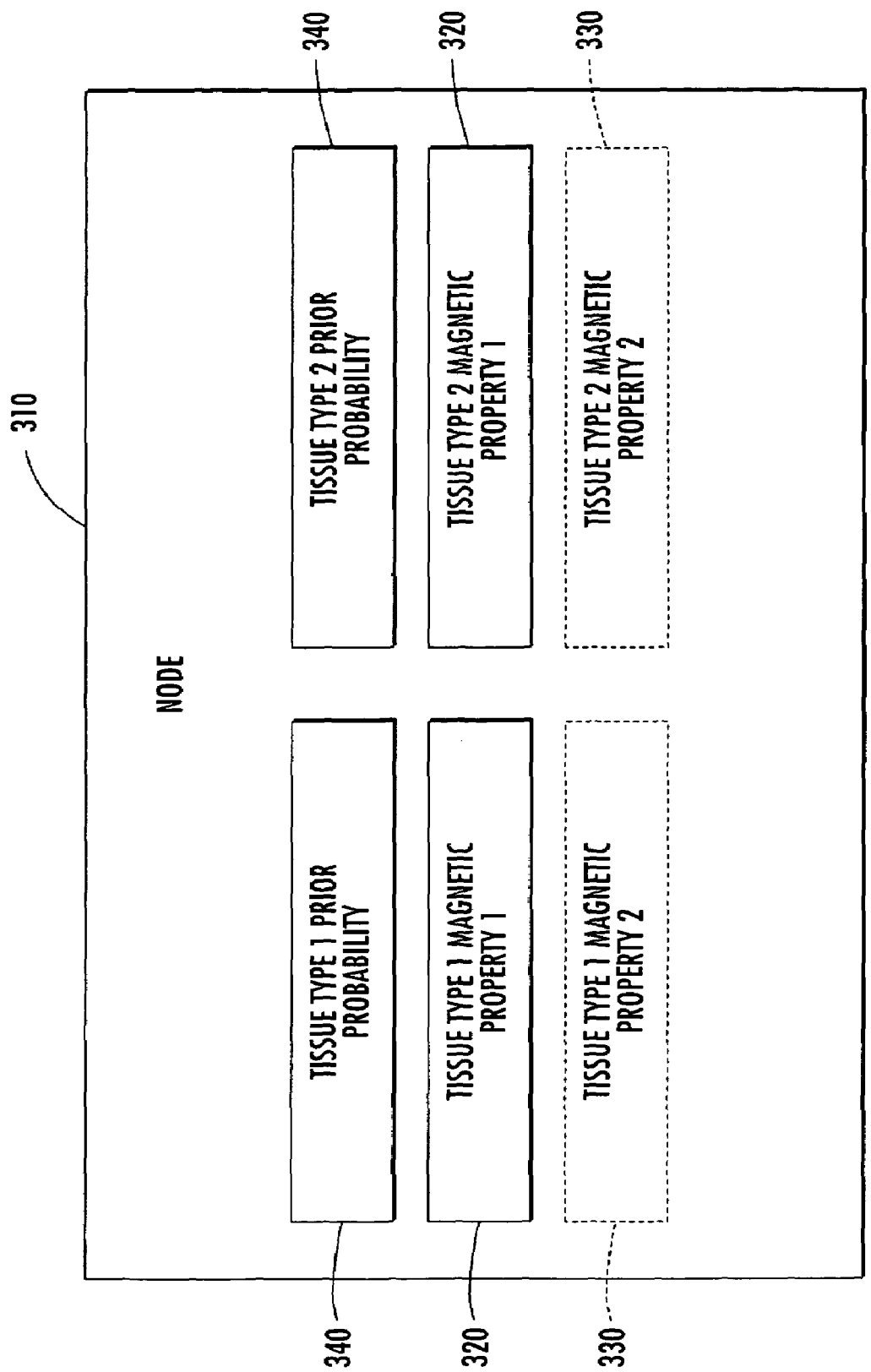

In a further embodiment, illustrated by way of example in FIG. 6, a tissue type prior probability 340 may be stored at a node 310 for each tissue type located at a corresponding voxel 210. A magnetic property 320 is also stored at the node 310 for each tissue type. Optionally, one or more further magnetic properties 330 may also be stored at the node 310.

Figure 7:
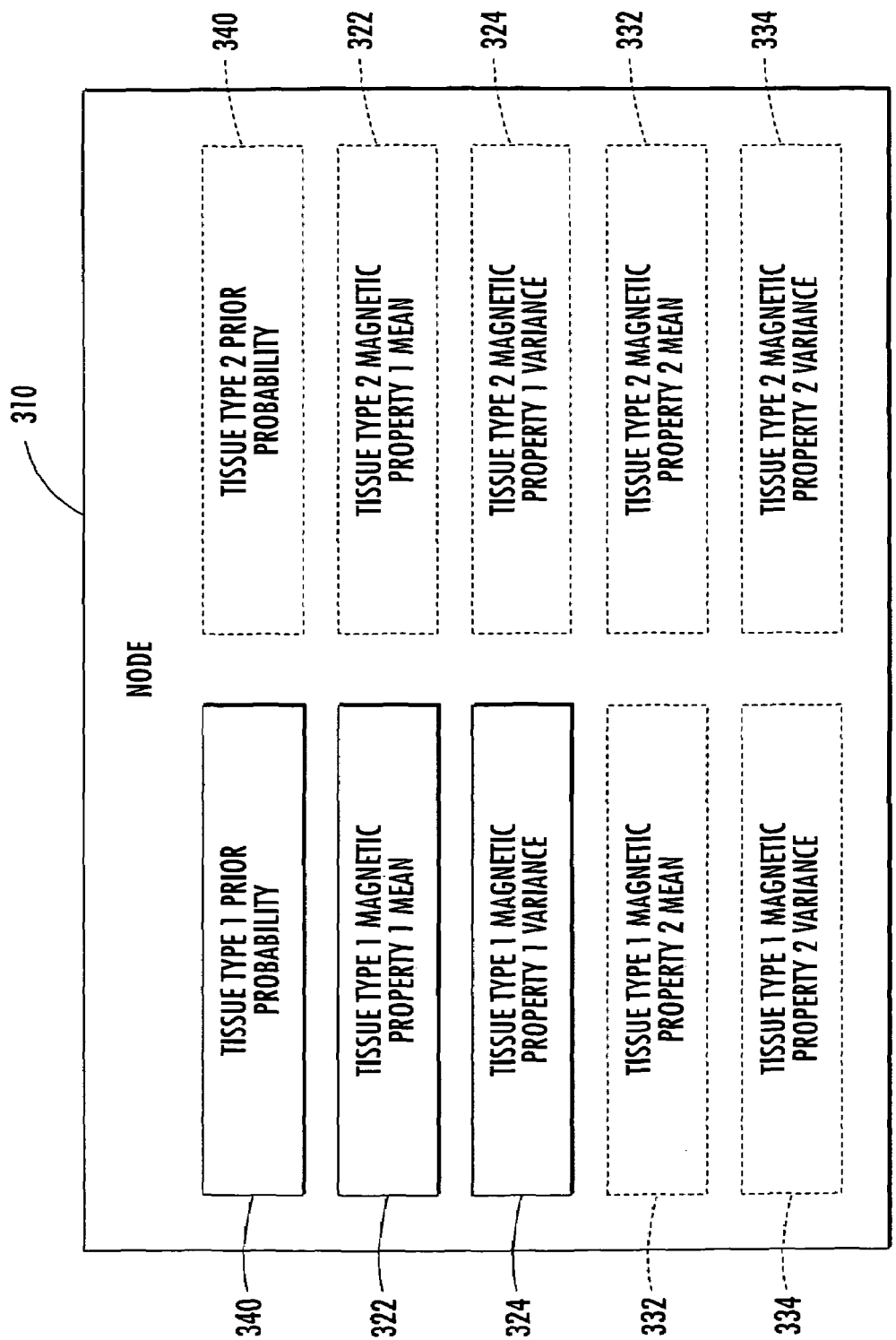

A further embodiment of a node 310 is illustrated in FIG. 7. The node 310 of FIG. 7 provides a tissue type prior probability 340 and statistical data pertaining to a magnetic property of the tissue of a corresponding voxel 210, relative to a plurality of subjects. As shown by way of example in FIG. 7, a mean 322 of the values of a first magnetic property for a first tissue type at the corresponding voxel 210 is provided. A variance 324 of the values of a first magnetic property for the first tissue type at the corresponding voxel 210 is also provided.

The node 310 of FIG. 7 may also optionally include statistical data pertaining to one or more additional magnetic properties, such as a mean 332 and variance 334 of a second magnetic property.

The node 310 of FIG. 7 is also optionally suitable for use with an atlas 300 containing information from a plurality of subjects 100. Any of the data 322, 324, 332, 334, 340 as described above in relation to a first tissue type, may also be determined in relation to a second tissue type and stored.

Figure 8:
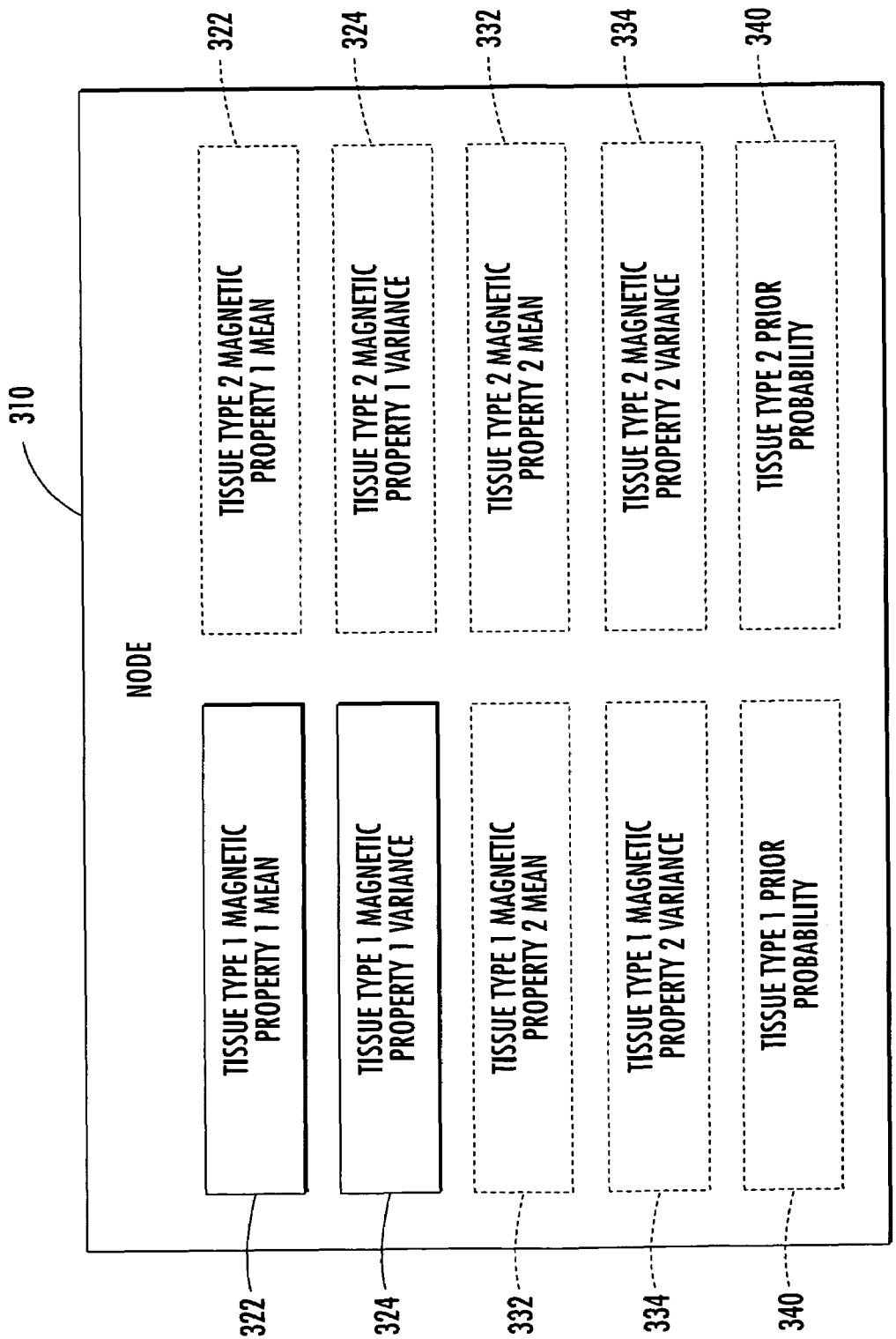

FIG. 8 illustrates a node 310 of a further embodiment of the invention providing statistical data, such as a mean 322 and a variance 324, of the values of a first magnetic property for a first tissue type at a corresponding voxel 210. Optionally, further statistical data 332, 334 or a tissue type prior probability 340 may be provided. Similar information 322, 324, 332, 334, 340 may also be optionally provided relating to further tissue types at a corresponding voxel 210.

As illustrated by way of example in FIGS. 9A and 9B, the determination of a mean 322 and a variance 324 for a first magnetic property can be determined. FIG. 9A provides a table 400 having the sample magnetic property values for an analogous voxel of each of three subjects. FIG. 9B illustrates the three steps 410, 420, 430 involved in determining the content of the node 310 corresponding to the illustrative voxel. As shown in step 1,410, the tissue type is 1, the mean of the value is 100 and the variance is 0. The prior probability of this node corresponding to a voxel of tissue type 1 is 1. Step 2,420, adds the data of the second subject to the data already tabulated from the first subject. Therefore, the mean now rises to 150, while the remaining data is unchanged, as the tissue type is 1 for both subjects, leaving the prior probability at 1.

Step 3,430, illustrates a node configuration illustrated in FIG. 7 or 8 by the tabulation of statistical data per tissue type for each node. Because the tissue type for the third subject is 2, a second set of statistical data is tabulated for the new tissue type, while the first set of data is updated in view of the third subject. The mean and variance of tissue type 1 remain unchanged. The prior probability of tissue type 1, however, now changes to ⅔. The mean of tissue type 2 is 50, and the variance 0. The prior probability of tissue type 2 is ⅓.

In another embodiment, additional data may be stored at each node relating to the corresponding voxel or a representation thereof. For example, image intensity data, expressed in arbitrary units, may be stored. Alternatives include those apparent to one of skill in the art.

In another embodiment, global prior probabilities may be stored in the atlas of the present invention. Global probabilities indicate the overall prior probability of something, such as a tissue type appearing in a particular area, or anywhere, in a subject. The global mean and variance of various magnetic properties may also be determined and stored for each tissue type. Such global values may be stored at a variety of locations in the atlas, such as in a header, or alternatively, at each node.

Figure 10:
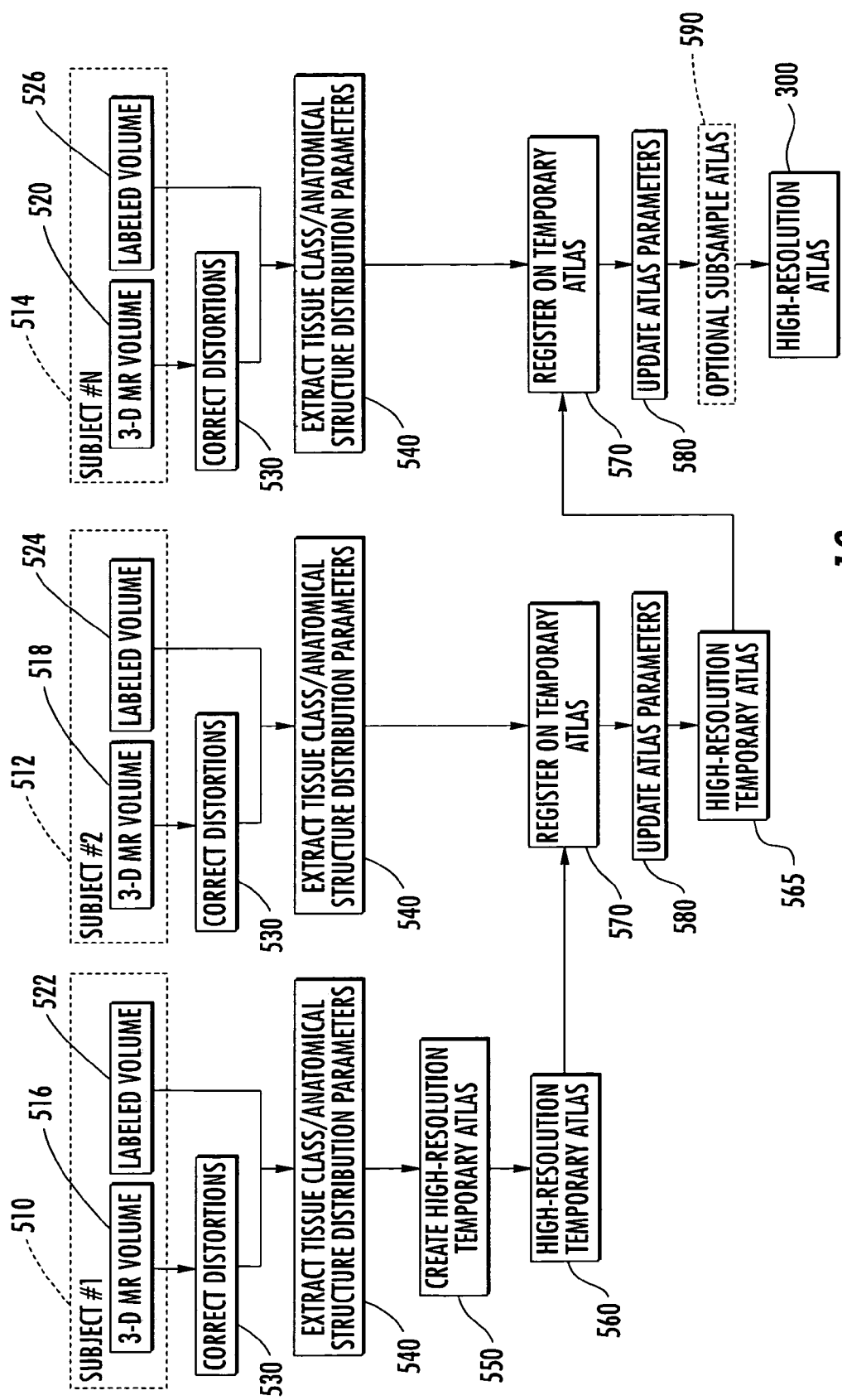
FIG. 10 provides a sample method for the creation of an atlas.

As shown by way of example in FIG. 10, a method 500 is provided according to an embodiment of the invention for the creation of an atlas 300. The atlas is built from one or more subject data sets 510, 512, 514. A subject data set may contain at least one MR scan 516, 518, 520 of a subject (e.g. an organ or a portion of an organ). The MR scans can be, but are not limited to, T1, T2, proton density (PD), T2*, magnetization transfer, diffusion tensor or derived variables such as anisotropy and diffusivity.

Distortions are then corrected in the MR scan 516, step 530. Corrections of distortion are known to one of ordinary skill in the art and are discussed in more detail in relation to FIG. 11 herein.

According to one embodiment, a subject's data set used in creating or adding to an atlas can also contain a labeled representation 522, 524, 526 of the MR scan(s), such as a segmented volume identifying each tissue type/anatomical structure. The labeled representation can be obtained by way of manual labeling (e.g. by experienced anatomists) and/or by way of automatic segmentation methods as described by way of example in Wells, supra, *Statistical Approach to Segmentation of Single-Channel Cerebral MR Images*, Rajapakse J C, et al., *IEEE Transactions on Medical Imaging*, 1997, Vol. 16, No.2: 176-86, and *Automated Model-Based Bias Field Correction of MR Images of the Brain*, Van Leemput, K. et al., *IEEE Transactions on Medical Imaging*, 1999, Vol. 18, No. 10, which are incorporated herein by reference.

Next, the tissue type and corresponding magnetic property statistical distribution data is extracted from the corrected subject data set 510, step 540.

A high-resolution temporary atlas 560, step 550, is then created by storing the tissue type and corresponding magnetic property statistical data of each voxel 210 of the subject, in each corresponding node 310 of the atlas 300.

The high-resolution temporary atlas 560 may then be used as the atlas 300 if the atlas 300 is to only have data pertaining to a single subject.

However, if additional subjects are to be added, the method 500 continues with the subject data set 512 of a second subject, and, optionally subject data sets 514 of additional subjects. Correction of distortion, step 530, and extraction of statistical data 540 is conducted as in relation to the first subject data set 510.

After each additional subject data set 512, 514 is processed, the tissue type and corresponding magnetic property statistical data of each voxel 210 of the subject is registered, or aligned, with the existing node structure of the atlas 300, step 570. During registration, the data, such as tissue type and magnetic statistical data, corresponding to the voxels 210 of the subject, is manipulated to correspond to the analogous voxels 210 represented by the node 310 structure of the atlas. Further details of registration, step 570, are discussed in detail in relation to FIG. 11 herein.

Next, the additional data, such as tissue type and magnetic statistical data, is then added to the atlas 300 by updating the atlas parameters, step 580. As shown in FIG. 10, a high-resolution atlas 565 is produced after the addition of two subject data sets 510, 512 to the atlas 300. This high-resolution atlas 565 may be used as an atlas 300, or additional subject data sets 514 may be added.

When the desired N subject data sets have been added to the atlas, the atlas may optionally be subsampled, step 590 to create the atlas 300. As discussed herein, alternatives of the invention may involve fewer nodes 310 than voxels 210. In such a case, a node 310 may be configured to represent a plurality of voxels 210 or the nodes 310 may represent only a subset of the overall voxels 210. Such a reduced resolution may also be generated by the subsampling, step 590, by combining data from multiple voxels into one node. Also, only a portion of the voxels representing a portion of the subject may be used in the atlas 300.

An atlas 300 of the present invention may be customized for a specialized purpose. The atlas may have values of a statistical representation that are population-specific (e.g., related to age, sex and/or pathology), scanner-specific (e.g., related to manufacturer and/or scanner model), and/or acquisition sequence-specific (e.g., related to flash and/or inversion recovery). Acquisition sequences can include including, without limitation, at least one from the group of PD-, T2-, T1-, diffusion-, and magnetization transfer-weighted. Acquisition sequence-specific values may involve magnetic resonance sequence parameters, including, without limitation, at least one from the group of TR, TE and flip angle.

An atlas of the present invention may be oriented to various coordinate systems. One such example of a coordinate system is a Cartesian coordinate system, such as a Right Anterior Superior (RAS) coordinate system, used in orienting an image relative to a subject, or an arbitrarily determined coordinate system.

An atlas of the present invention may be created at various spatial resolutions. An atlas may further be sub-sampled to reduce the resolution and data required and time required for calculations. The resolution may also vary within an atlas, allowing greater resolution at areas of interest.

Figure 11:
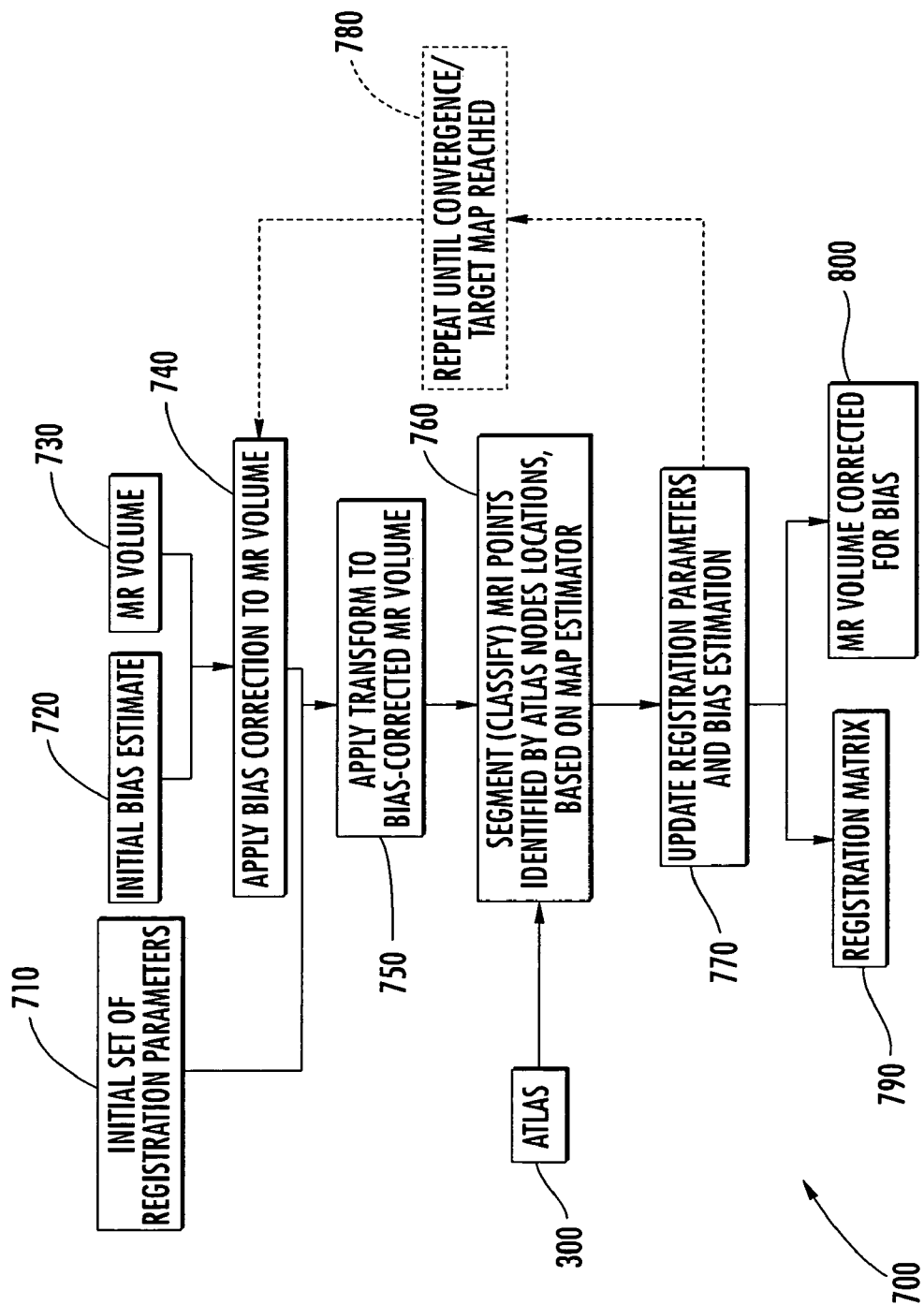
FIG. 11 provides a sample method for the registration of MR data to an atlas.

According to one embodiment of the invention, an atlas may be constructed as shown in FIGS. 10 and 11. Optionally, an atlas may be formed by data from only one subject. An atlas may be formed by N subjects, which may be determined by monitoring the change of values within the atlas upon the addition of each additional subject. According to another embodiment, when the values stored in the nodes of the atlas no longer vary within a statistical range of confidence, the addition of further subjects is no longer required.

The registration of data onto the atlas may comprise the determination of at least 6 parameters. For example, those parameters can be 3 translation shifts, 3 scaling factors and 3 rotation angles relatively to the 3 orthogonal directions of the atlas coordinate system.

Further detail regarding registration of data onto an atlas, or temporary atlas as described in FIG. 10, is illustrated by way of example in the method 700 of FIG. 11. In FIG. 11, a method 700 is provided according to an embodiment of the invention for the registration of MR data to an atlas 300. The example method 700 of FIG. 11 is also applicable to prior probability data or any other data types for association to nodes 310 of the atlas 300.

An initial set of registration parameters is provided, step 710, along with an initial bias estimate, step 720, according to methods known to one of skill in the art in relation to atlases having other types of data. See, for example, Wells, supra, *Automated Model-Based Bias Field Correction of MR*

Images of the Brain, Van Leemput, K. et al., *IEEE Transactions on Medical Imaging*, 1999, Vol. 18, No. 10, and *Automatic Scan Prescription for Brain MRI*, Itti, L. et al., *Magnetic Resonance in Medicine*, 2001, Vol. 45: 486-494, which are incorporated herein by reference. The initial bias estimate of step 720 adjusts for intensity fall-off in the portions of the image away from the image center.

A magnetic resonance (MR) volume is also provided, step 730. The magnetic resonance volume can be generated by deriving a magnetic property value for a voxel from a voxel intensity value of a corresponding voxel of an image containing magnetic resonance data.

A bias correction is applied to the MR volume, step 740. With regard to step 740, and step 530 of FIG. 10, distortion and bias can be caused by a variety of factors. For example, the distortion and bias can be subject-dependent, such as from, but not limited to, chemical shift, magnetic susceptibility, and/or per-acquisition motion. Alternatively or in addition, distortion and bias can be scanner-dependent, such as from, but not limited to, gradients non-linearity, main magnetic field non-homogeneity and/or eddy currents. Maxwell effects are a further source of potential distortion or bias.

Correction of such distortion and bias are known to one of ordinary skill in the art.

As shown in FIGS. 10 and 11, bias and distortion are corrected prior to incorporating the data into the atlas. According to a further embodiment of the invention, distortion and bias are corrected prior to processing data in conjunction with the atlas.

A transform is applied to the bias-corrected MR volume, step 750. Linear transformations (e.g. translation, rotation, scaling) are applied to images via homogeneous matrices. According to one embodiment, they are 4×4 matrices, wherein the 3 first bottom elements always equal 0 and the last bottom elements always equals 1. Any transformation can be decomposed into a translation, a rotation and a scaling matrices. The final homogeneous matrix is then a multiplication of those 3 matrices. Details are given by way of example below:

tx, ty and tz being the translation parameters in the x, y and z directions, the translation homogeneous matrix is given by:

$$\begin{pmatrix} 1 & 0 & 0 & t_x \\ 0 & 1 & 0 & t_y \\ 0 & 0 & 1 & t_z \\ 0 & 0 & 0 & 1 \end{pmatrix}$$

xs, ys and zs being the scaling parameters in the x, y and z directions, the scaling homogeneous matrix is given by:

$$\begin{pmatrix} x_s & 0 & 0 & 0 \\ 0 & y_s & 0 & 0 \\ 0 & 0 & z_s & 0 \\ 0 & 0 & 0 & 1 \end{pmatrix}$$

θ, φ and ϕ being the rotation parameters relatively to the x, y and z axis, the rotation homogeneous matrix is given by:

$$\begin{pmatrix} \cos\varphi\cos\phi + \sin\varphi\sin\theta\sin\phi & \sin\varphi\cos\theta - \cos\varphi\sin\theta\sin\phi & \cos\theta\sin\varphi & 0 \\ -\sin\varphi\cos\theta & \cos\varphi\cos\theta & \sin\theta & 0 \\ \sin\varphi\sin\theta\cos\phi - \cos\varphi\sin\theta & -\cos\varphi\sin\theta - \sin\varphi\sin\theta & \cos\theta\cos\varphi & 0 \\ 0 & 0 & 0 & 1 \end{pmatrix}$$

The voxels, or MRI points, corresponding to nodes 310 of the atlas 300 are segmented based on a Maximum A Posteriori (MAP) estimator, step 760. The MAP estimator is a probability computation with statistical information stored in the atlas. The MAP estimator and its use with other types of data are known to one of ordinary skill in the art, as illustrated by way of example in Wells, supra, *Statistical Approach to Segmentation of Single-Channel Cerebral MR Images*, Rajapakse J C, et al., *IEEE Transactions on Medical Imaging*, 1997, Vol. 16, No.2: 176-86, and *Automated Model-Based Bias Field Correction of MR Images of the Brain*, Van Leemput, K. et al., *IEEE Transactions on Medical Imaging*, 1999, Vol. 18, No. 10, which are incorporated herein by reference.

The registration parameters and bias estimation are then updated, step 770, as is known to one of ordinary skill in the art, as illustrated by way of example in Wells, supra, *Automated Model-Based Bias Field Correction of MR Images of the Brain*, Van Leemput, K. et al., *IEEE Transactions on Medical Imaging*, 1999, Vol. 18, No. 10, and *Multimodality Image Registration by maximization of Mutual Information*, Maes, F. et al., *IEEE Transactions on Medical Imaging*, 1997, Vol. 16, No. 2, which are incorporated herein by reference. If the target MAP is not reached, the process repeats, step 780, beginning again with application of bias correction to the MR volume, step 740.

If the target MAP is reached, the registration matrix is provided, step 790. The registration matrix can include sixteen (16) values, including translation parameters, scaling parameters, and a combination of the sines and cosines of rotation parameters. The registration matrix can be used to obtain a specific geometry (e.g. orientation and/or dimensions) of the data acquired during a subsequent scan, as discussed herein.

The MR volume corrected for bias is also provided, step 800, allowing more accurate computation of the magnetic property values for each node of the atlas.

Further information regarding the details of the steps of FIG. 11 can be found in Wells, supra, *Automated Model-Based Bias Field Correction of MR Images of the Brain*, Van Leemput, K. et al., *IEEE Transactions on Medical Imaging*, 1999, Vol. 18, No. 10, and *Multimodality Image Registration by maximization of Mutual Information*, Maes, F. et al., *IEEE Transactions on Medical Imaging*, 1997, Vol. 16, No. 2, which are incorporated herein by reference.

Figure 12:
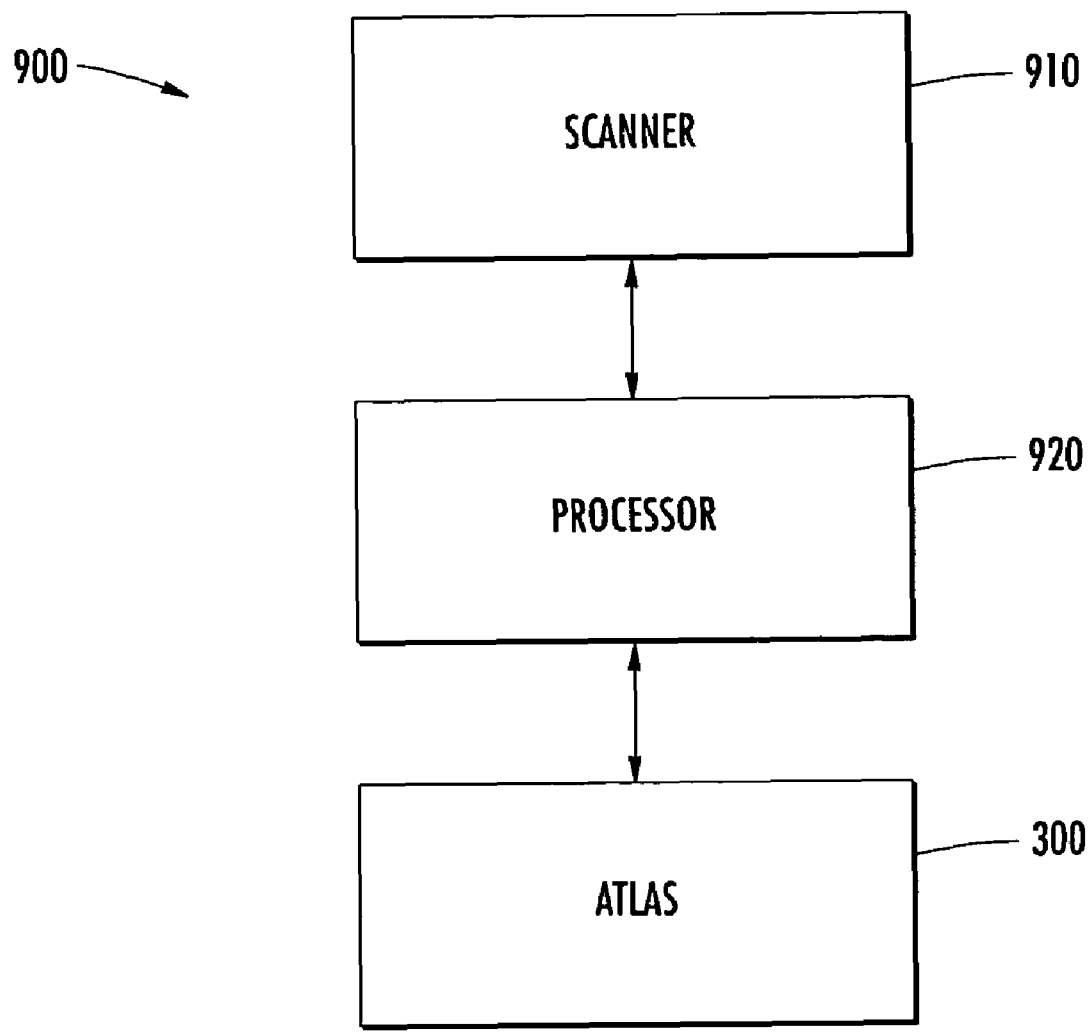
FIG. 12 provides a functional schematic of a system according to an embodiment of the invention.

According to a further embodiment of the invention, a system 900 is provided as shown by way of example in FIG. 12. A scanner 910 is provided to capture magnetic images. A processor 920 is provided to interface with the scanner 910 and the atlas 300 in order to conduct the methods according to various embodiments of the present invention.

The atlas and system 900 of the present invention may be used in a variety of applications. In one embodiment, a method of using the atlas with magnetic property data and optionally with tissue (or anatomical structure) type prior probabilities is provided, automatically align an MR scan, such as a localizer scan, to obtain a specific geometry of the data acquired during a subsequent scan (auto-slice prescription). Further details of this implementation can be found in U.S. Pat. No. 6,195,409, issued Feb. 27, 2001, to Chang et al., which is incorporated herein by reference.

In an additional embodiment, a method of using the atlas with magnetic property data to determine anatomical structure or detect abnormal tissue (auto-segmentation) is provided. Further details of this implementation can be found in Wells, supra, *Statistical Approach to Segmentation of Single-Channel Cerebral MR Images*, Rajapakse J C, et al., *IEEE Transactions on Medical Imaging*, 1997, Vol. 16, No.2: 176-86, and *Automated Model-Based Bias Field Correction of MR Images of the Brain*, Van Leemput, K. et al., *IEEE Transactions on Medical Imaging*, 1999, Vol. 18, No. 10, which are incorporated herein by reference.

It will further be appreciated that in the methods of the present invention, including the applications described herein, distortion of newly obtained data may optionally be corrected prior to processing data in conjunction with the atlas. Further details of distortion correction can be found in *Sources of Distortion in Functional MRI Data*, Jezzard, P. et al., *Human Brain Mapping*, 1999, Vol. 8:80-85, which is incorporated herein by reference.

The present invention has been described by way of example, and modifications and variations of the described embodiments will suggest themselves to skilled artisans in this field without departing from the spirit of the invention. Aspects and characteristics of the above-described embodiments may be used in combination. The described embodiments are merely illustrative and should not be considered restrictive in any way. The scope of the invention is to be measured by the appended claims, rather than the preceding description, and all variations and equivalents that fall within the range of the claims are intended to be embraced therein. The contents of all references, databases, patents and published patent applications cited throughout this application are expressly incorporated herein by reference.

What is claimed is:

1. A method for obtaining information about a subject, comprising the steps of:
   providing a prior probability MRI based atlas having magnetic resonance data including tissue type prior probability derived from at least one other subject;
   processing with a processor information received from a magnetic resonance scanner pertaining to said subject, wherein said information includes data from a magnetic resonance scan;
   reading said atlas; and
   determining alignment of said magnetic resonance scan to obtain a specific geometry of a subsequent magnetic resonance scan.

2. The method of claim 1, further comprising the steps of:
   communicating alignment data from said processor to said scanner; and
   automatically aligning said magnetic resonance scan to obtain said specific geometry of a subsequent magnetic resonance scan by the use of said alignment data.

3. The method of claim 1, wherein said step of providing a prior probability MRI based atlas having magnetic property values derived from at least one other subject involves data derived from a plurality of subjects.

4. A method of using a processor for obtaining information about a subject, comprising the steps of:
   providing magnetic property values from a magnetic resonance scanner pertaining to said subject;
   providing a prior probability MRI based atlas having at least two magnetic property values for at least one corresponding voxel derived from at least one other subject; and
   labeling by said processor of tissue types of a tissue corresponding to said magnetic resonance property values pertaining to said subject by the use of said atlas having said magnetic resonance values derived from at least one other subject.

5. The method of claim 4, wherein said step of providing a prior probability MRI based atlas having magnetic property values derived from at least one other subject involves data derived from a plurality of other subjects.

6. A method for creating an a prior probability MRI based atlas, comprising the steps of:
   providing a first magnetic resonance modality volume pertaining to a subject and divided into voxels;
   correcting distortion of said first magnetic resonance modality volume;
   recording a magnetic property value in a node of said atlas corresponding to a voxel of said first magnetic modality volume;
   providing a second magnetic resonance modality volume pertaining to a second subject and divided into voxels;
   correcting distortion of said second magnetic resonance modality volume; and
   updating said magnetic property data in said node of said atlas corresponding to a voxel of said second magnetic resonance modality volume.

7. The method of claim 6, wherein the step of correcting involves the correction of distortion caused by at least one of the group consisting of chemical shift, magnetic susceptibility, per-acquisition motion, gradients non-linearity, main magnetic field non-homogeneity, eddy currents, and Maxwell effects.

8. The method of claim 6, further comprising the steps of:
   providing a plurality of magnetic resonance modality volumes pertaining to a plurality of subjects and each of said plurality of magnetic resonance modality volumes divided into voxels;
   correcting distortion of each of said plurality of magnetic resonance modality volumes; and
   updating said magnetic property value in said node of said atlas corresponding to a voxel of each of said plurality of magnetic resonance modality volumes;
   wherein said magnetic property value in said node of said atlas includes statistical data.

9. A method for creating a prior probability MRI based atlas, comprising the steps of:
   providing a first magnetic resonance modality volume pertaining to a subject and divided into voxels;
   providing a labeled volume indicating tissue types of tissue corresponding to said voxels;
   correcting distortion of said first magnetic resonance modality volume;
   extracting magnetic property distribution parameters for each tissue type identified at each voxel;
   recording magnetic property data corresponding to each tissue type in a node of said atlas corresponding to a voxel of said first magnetic resonance modality volume;
   providing a plurality of magnetic resonance modality volumes pertaining to a plurality of subjects and each of said plurality of magnetic resonance modality volumes divided into voxels;

providing a plurality of labeled volumes corresponding to said plurality of magnetic resonance modality volumes and indicating tissue types of tissue corresponding to said voxels;

correcting distortion of each of said plurality of magnetic resonance modality volume; and updating said magnetic property data in said node of said atlas corresponding to a voxel of each of said plurality of magnetic resonance modality volumes.

10. A method for obtaining information about a subject, comprising the steps of:

providing a prior probability MRI based atlas having magnetic resonance data including more than one magnetic property value prior probability derived from at least one other subject;

processing with a processor information received from a magnetic resonance scanner pertaining to said subject, wherein said information includes data from a magnetiC resonance scan;

reading said atlas; and determining alignment of said magnetic resonance scan to obtain a specific geometry of a subsequent magnetic resonance scan.

11. The method of claim 10 further comprising the steps of:

communicating alignment data from said processor to said scanner; and automatically aligning said magnetic resonance scan to obtain said specific geometry of a subsequent magnetic resonance scan by the use of said alignment data.

12. The method of claim 10, wherein said step of providing a prior probability MRI based atlas having magnetic property values derived from at least one other subject involves data derived from a plurality of subjects.

13. A method of aligning and/or segmenting an MR scan, the method comprising:

scanning a subject with an MR scanner to produce a magnetic resonance image;

interfacing the magnetic resonance image with a prior probability MRI based atlas, which includes nodes which each include: tissue type probability information, magnetic property values, and location information to determine, from the scan, the probability of tissue type by location in the magnetic resonance image; and aligning the MR scan and/or segmenting the MR scan.

14. A method of aligning and/or segmenting an MR scan, the method comprising:

providing a prior probability MRI based atlas from at least three MR scans of other subjects which define node locations in anatomic atlas space which are independent of MR imaging platform voxel properties whereas voxels are dependent upon MR imaging instrument instructions and nodes are independent of MR imaging platform instructions, each node including probability information for at least four independent properties: location in three dimensional atomic atlas space, prior probability of specific tissue types at this nodal location, statistics of at least one magnetic resonance property assigned to specific tissue types at this nodal location, and prior probability of specific tissue types of neighboring nodes for each tissue type at this nodal location, wherein magnetic resonance property values include one or more parameters such as $T_1$ or $T_2$ for the identical nodal location in anatomic space;

scanning a subject with an MR scanner to produce a magnetic resonance image representative of that subject comprised of voxel volume elements constructed in accordance with MR imaging instrument instructions;

interfacing the magnetic resonance image with the a priori nodal information from the atlas; and aligning the MR scan and/or segmenting the MR scan to maximize the post probability of its voxel components matching both position in anatomic space and at least one MR tissue characteristic of the nodes determined a priori in the atlas.

15. The method of claim 14 in which two MR scans are obtained at different points in time to develop data about changes in anatomic distribution of organ tissue components andlor changes in their MR properties independent of imaging instrument instructions.

16. A method of creating an a priori nodal atlas as a reference for the consistent alignment and/or segmentation of subsequent MR scans comprising:

assigning to each node of the atlas information about location in three dimensional anatomic space, as well as information about magnetic resonance properties of each location in anatomic space for specific tissue types and prior probability for specific tissue types and prior probability of specific tissue types of neighboring nodes for each tissue type at the nodal location.

17. A method of using an a priori nodal atlas as a reference for alignment and/or segmentation of subsequent MR scans comprising:

reading data from an MR scan;

reading an a priori nodal atlas wherein, each node of the atlas is based on at least 3 MRI scans and wherein the atlas contains information about location in three-dimensional anatomic space, as well as information about magnetic resonance properties of each location in anatomic space for specific tissue types, prior probability for specific tissue types, and prior probability for specific tissue types of neighboring nodes for each tissue type at the nodal location; and aligning and/or segmenting subsequent scans by operating on voxel based images created in accordance with instructions of an imaging instrument and applying transformations which maximize the probability of matching each voxel to a corresponding node in the atlas.

18. A system for obtaining information about a subject, the system comprising:

a processor adapted to receive information obtained from a magnetic resonance scan and read a prior probability MRI based atlas to determine a tissue type the prior probability MRI based atlas comprising:

a plurality of nodes corresponding to a plurality of voxels representing spatial locations of a subject, each of said nodes configured to store at least one magnetic property value as determined by magnetic resonance imaging at least one tissue type prior probability value corresponding to a tissue type of a voxel, thereby determining the tissue type.

* * * * *